US006790191B1

(12) United States Patent
Hendricks

(10) Patent No.: US 6,790,191 B1
(45) Date of Patent: Sep. 14, 2004

(54) HYPEREXTENSION BACK BRACE SYSTEM

(76) Inventor: David J. Hendricks, 26834 Carla Pl., Lutz, FL (US) 33549

( * ) Notice: Subject to any disclaimer, the term of this patent is extended or adjusted under 35 U.S.C. 154(b) by 0 days.

(21) Appl. No.: 09/437,854

(22) Filed: Nov. 10, 1999

(51) Int. Cl.$^7$ ................................................. A61F 5/02
(52) U.S. Cl. ..................................... 602/19; 128/102.1
(58) Field of Search ............................... 602/19, 5, 16; 128/95.1, 96.1, 98.1, 99.1, 100.1, 101.1, 102.1, 103.1, 104.1, 105.1, 106.1–107.1, 108.1, 111.1, 112.1, 117.1, 121.1, 123.1, DIG. 19; 2/44, 45

(56) References Cited

U.S. PATENT DOCUMENTS

| | | | | | |
|---|---|---|---|---|---|
| 639,072 | A | * | 12/1899 | Lyones | .................... 602/19 |
| 1,948,785 | A | * | 2/1934 | Dondelinger | ............ 128/108.1 |
| 1,981,157 | A | * | 11/1934 | Walter | .................... 128/99.1 |
| 2,293,998 | A | * | 8/1942 | Norwood | ................ 128/102.1 |
| RE31,564 | E | * | 4/1984 | Hendricks | .................... 602/19 |
| 4,640,269 | A | * | 2/1987 | Goins | .......................... 602/19 |
| 4,648,390 | A | * | 3/1987 | Friddle | ........................ 602/19 |
| 5,135,471 | A | * | 8/1992 | Houswerth | .................... 602/19 |
| 5,674,187 | A | * | 10/1997 | Zepf | .......................... 602/19 |
| 6,010,472 | A | * | 1/2000 | Schiller | ...................... 602/19 |

* cited by examiner

*Primary Examiner*—Nicholas D. Lucchesi
*Assistant Examiner*—Huong Q. Pham
(74) *Attorney, Agent, or Firm*—Myers & Kaplan LLC; Sandra M. Sovinski; Joel D. Myers

(57) ABSTRACT

A hyperextension back brace system is a cruciform structure with an upper and lower vertical arms, left and right horizontal arms, and an extender arm for each of the arms. A pubic pad has an inwardly facing resilient foam fixedly coupled to the lower end of the extender arm of the lower vertical arm. A V-shaped intermediate plate is secured at its central extent to the upper end of the extender arm of the upper vertical arm with a pair of pectoral pads. The V-shaped plate has upwardly extending arms. A pair of rigid side pads have an inwardly facing resilient foam fixedly coupled to the exterior end of the horizontal extender arms. A belt of a pile material is attached at one end of one of the side pads.

17 Claims, 4 Drawing Sheets

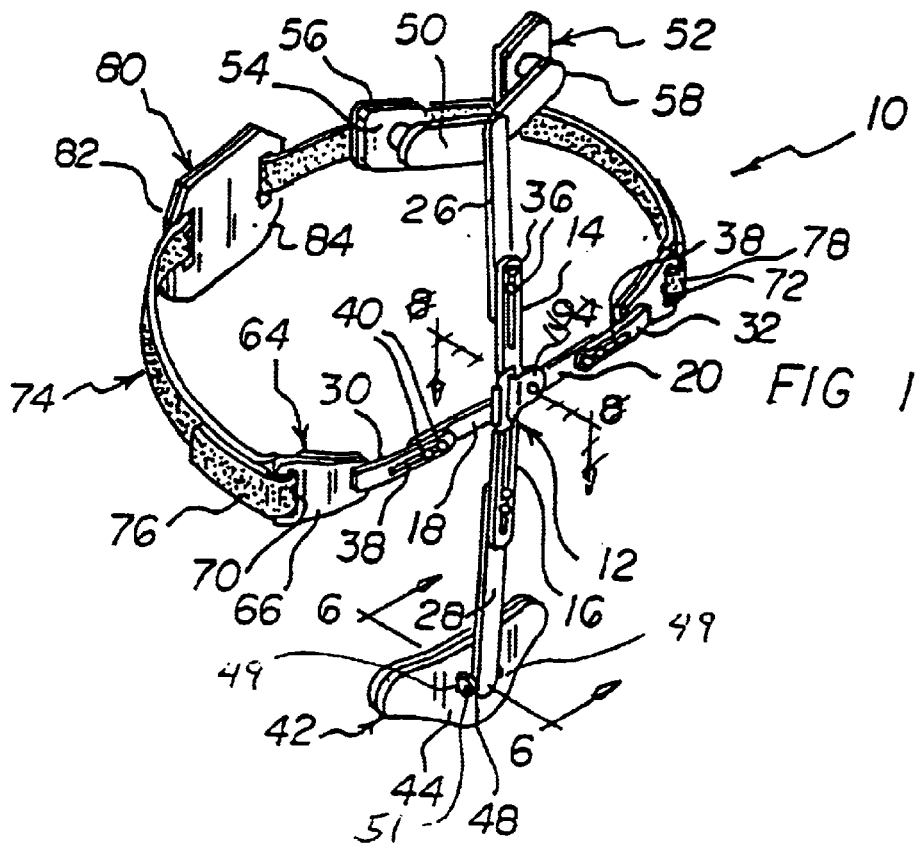
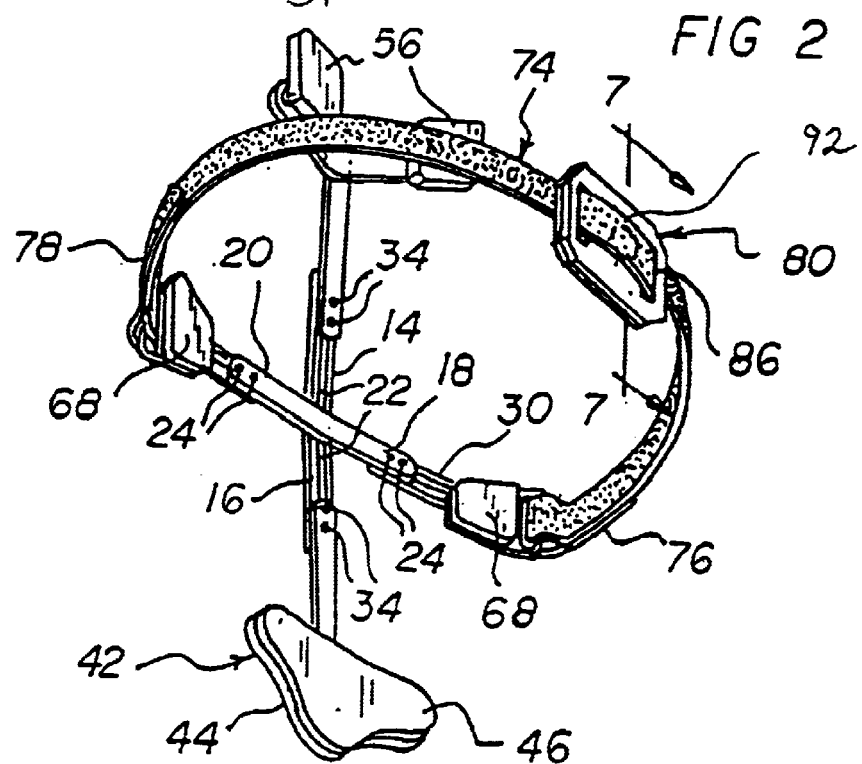

HYPEREXTENSION BACK BRACE SYSTEM

BACKGROUND OF THE INVENTION

1. Field of the Invention

The present invention relates to a hyperextension back brace system and more particularly pertains to applying pressure to the pubic area below and to spaced pectoral areas above and to the back thereby tending to extend the spine of a user.

2. Description of the Prior Art

The use of brace systems of known designs and configurations is known in the prior art. More specifically, brace systems of known designs and configurations heretofore devised and utilized for the purpose of applying pressure to points of a wearer through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. Re. 31,564 to Hendricks discloses a hyperextension back brace. U.S. Pat. No. 2,582,930 to Jewett discloses a surgical brace. U.S. Pat. No. 2,808,050 to Ward discloses a surgical brace. U.S. Pat. No. 4,640,269 to Goins discloses a back brace having strap with widened middle portion for pad. U.S. Pat. No. 4,976,257 to Akin et al discloses a hyperextension brace. U.S. Pat. No. 5,135,471 to Houswerth discloses a cruciform anterior spinal hyperextension orthosis. U.S. Pat. No. 5,342,289 to Munny discloses a hyperextension orthosis with movable front pad. Lastly, U.S. Pat. No. 5,632,724 to Lerman et al. discloses a hyperextension thoraco-lumbar brace.

The hyperextension back brace system according to the present invention substantially departs from the conventional concepts and designs of the prior art, and in doing so provides an apparatus primarily developed for the purpose of applying pressure to the pubic area below and to spaced pectoral areas above and to the back thereby tending to extend the spine of a user.

Therefore, it can be appreciated that there exists a continuing need for a new and improved hyperextension back brace system which can be used for applying pressure to the pubic area below and to spaced pectoral areas above and to the back thereby tending to extend the spine of a user. In this regard, the present invention substantially fulfills this need.

SUMMARY OF THE INVENTION

In view of the foregoing disadvantages inherent in the known types of brace systems of known designs and configurations now present in the prior art, the present invention provides an improved hyperextension back brace system. As such, the general purpose of the present invention, which will be described subsequently in greater detail, is to provide a new and improved hyperextension back brace system and method which has all the advantages of the prior art and none of the disadvantages.

To attain this, the present invention essentially comprises a cruciform structure. The cruciform structure has an integrally formed upper vertical arm, a lower vertical arm, an integrally formed left horizontal arm and a right horizontal arm, wherein all such arms are couple together in a central area. A longitudinal slot is provided through the upper and lower vertical arms. A pair of threaded apertures is provided in each of the horizontal arms. An extender arm is provided for each of the arms of the cruciform structure. The extender arms for the vertical arms have a pair of threaded apertures with a pair of bolts extending through the slot for adjustable coupling with respect to the vertical arms. The extender arms for the horizontal arms have longitudinal slots. Bolts extend through extender arms for adjustable coupling with respect to the horizontal arms. Next provided is a public pad formed of a rigid aluminum material. The public pad has an inwardly extender arm. A pair of diamond-shaped pectoral pads are fabricated of a rigid aluminum material. Resilient form extends inwardly from the pectoral pads. Each pectoral pad is adjustably couple to a free end of the intermediate support through a foam rubber disc. One surface of each foam rubber disc includes a pile fastener and another surface of each disc is glued to one of the pectoral pads for coupling the pectoral pads to the V-shaped intermediate plate and for enabling universal swiveling. The flexible sponginess and natural resiliency inhindered universal swiveling and natural self-centering of each of the pectoral pads relative to the V-shaped intermediate plate. A pair of side pads are formed of a rigid material. The side pads are fixedly coupled to the exterior end of the horizontal extender arms. The side pads have an inwardly facing resilient foam. Each of the side pads has a vertical slot at its free end. A belt of a pile type material is attached at one end through a slot in one of the side pads and a free end adapted to be adjustably threaded through the other vertical slot. In this manner the belt is releaseably secured around the torso of a wearer. A back pad is fabricated of a semi-rigid plastic material. A resilient foam is provided and faces inwardly from the back pad. Vertical slots are provided in(the back pad at laterally disposed end locations adjacent the edges of the back pad for the passage of an intermediate portion of the belt. The back pad also includes a pile type locking strip coupled at its free end to the back pad. An intermediate extent is adapted to be releaseably secured to a pile type fastener on the back pad for the releasable securement. In this manner lateral shifting of the back pad of the belt is precluded. Lastly, a supplemental keeper is secured to one horizontal extender arm. The supplemental keeper has a vertical aperture. The keeper is adapted to removably receive the free end of the belt for further adjustment purposes.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved hyperextension back brace system which has all of the advantages of the prior art braces and supports and none of the disadvantages.

It is another object of the present invention to provide a new and improved hyperextension back brace system which may be easily and efficiently manufactured and marketed.

It is further object of the present invention to provide a new and improved hyperextension back brace system which is of durable and reliable constructions.

An even further object of the present invention is to provide a new and improved hyperextension back brace system which is susceptible of a low cost of manufacture with regard to both materials and labor, and which accordingly is then susceptible of low prices of sale to the consuming public, thereby making such hyperextension back brace system economically available to the buying public.

Even still another object of the present invention is to provide a hyperextension back brace system for applying pressure to the pubic area below and to spaced pectoral areas above and to the back thereby tending to extend the spine of a user.

Lastly, it is an object of the present invention to provide a new and improved hyperextension back brace system of a cruciform shape having an upper vertical arm, a lower vertical arm, a left horizontal arm, a right horizontal arm, and an extender arm for each of the arms. A pubic pad, formed of a rigid material with an inwardly facing resilient foam, is fixedly coupled to the lower end of the lower extender arm with a horizontal pivot pin. A V-shaped intermediate plate is secured at its central extent to the upper end of the upper extender arm. A pair of pectoral pads fabricated of a rigid aluminum material with an inwardly facing resilient foam extend inwardly from the intermediate plate. A pair of side pads, formed of a rigid material with an inwardly facing resilient foam, are fixedly coupled to the exterior end of the horizontal extender arms. Each of the side pads has a vertical slot at its free end. A belt of a pile type material is attached at one end through a slot of one of the side pads and a free end is adapted to be adjustably threaded through the other vertical slot. A back pad, fabricated of a semi-rigid plastic material with a resilient foam facing inwardly, has vertical slots at laterally disposed end locations adjacent the edges of the back pad.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the new and improved hyperextension back brace system constructed in accordance with the principles of the present invention.

FIG. 2 is a perspective illustration similar to FIG. 1, but taken from the rear thereof.

The same reference numerals refer to the same parts through the various Figures.

DESCRIPTION OF THE PREFERRED EMBODIMENT

Figure 3:
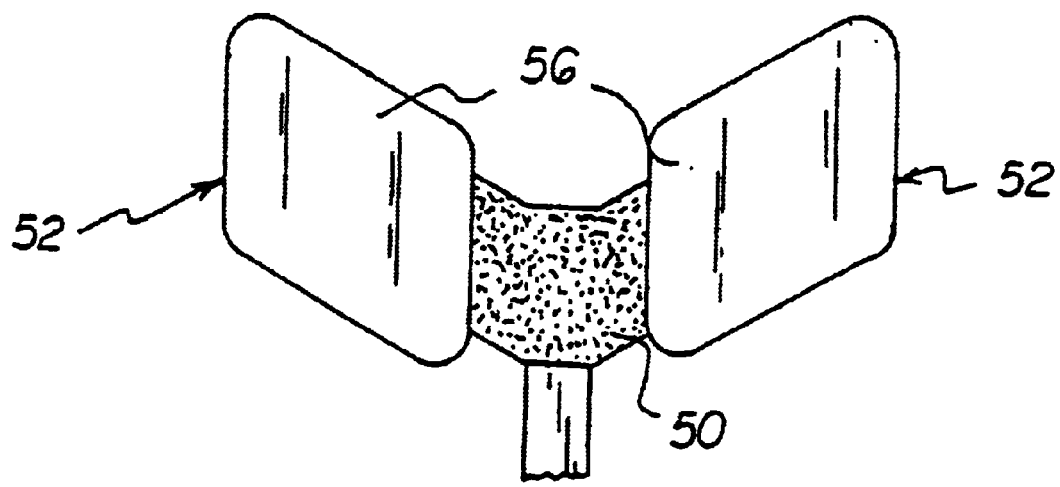
FIG. 3 is a rear elevational view of the upper region of the system shown in FIG. 1.
Figure 4:
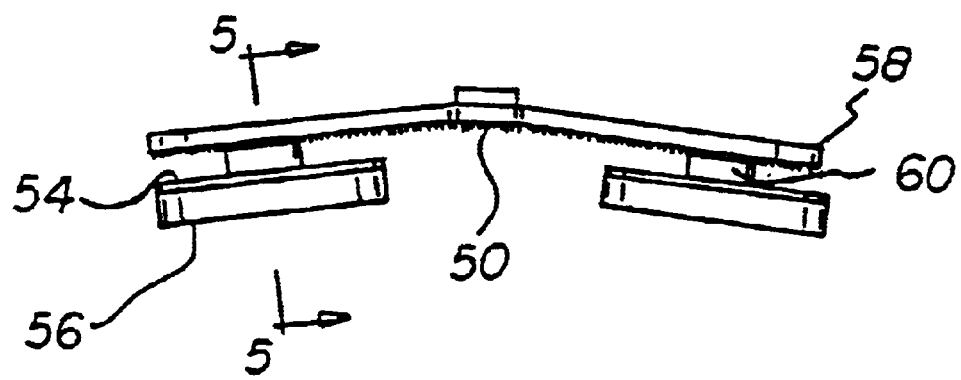
FIG. 4 is a top plan view of the upper region of the system shown in FIGS. 1 and 3.
Figure 5:
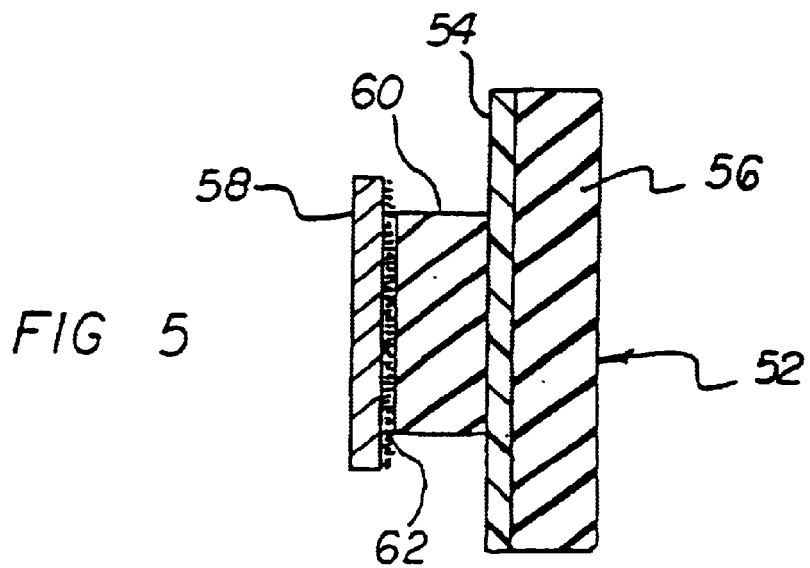
FIG. 5 is a cross sectional view taken along line 5—5 of FIG. 4.

With reference now to the drawings, and in particular to FIG. 1 thereof, the preferred embodiment of the new and improved hyperextension back brace system embodying the principles and concepts of the present invention and generally designated by the reference numeral 10 will be described.

The present invention, the hyperextension back brace system 10 is comprised of a plurality of components. Such components in their broadest context include a cruciform structure, a pubic pad, a V-shaped intermediate plate, a pair of side pads, a belt, a back pad, and a supplemental keeper. Such components are individually configured and correlated with respect to each other so as to attain the desired objective.

A cruciform structure 12 has an integrally formed upper vertical arm 14 and a lower vertical arm 16 and an integrally formed left horizontal arm 18 and a right horizontal arm 20 coupled together in a central area. A longitudinal slot 22 is provided through the upper and lower vertical arms. A pair of threaded apertures 24 are provided in each of the horizontal arms. An extender arm 26, 28, 30, 32 is provided for each of the arms of the cruciform structure. The extender arms for the vertical arms 26, 28 have a pair of threaded apertures 34 with a pair of bolts 36 extending through the slot for adjustable coupling with respect to the vertical arms. The extender arms 30, 32 for the horizontal arms 18, 20 have longitudinal slots 38. Bolts 40 extend through extender arms 30, 32 for adjustable coupling with respect to the horizontal arms.

Figure 6:
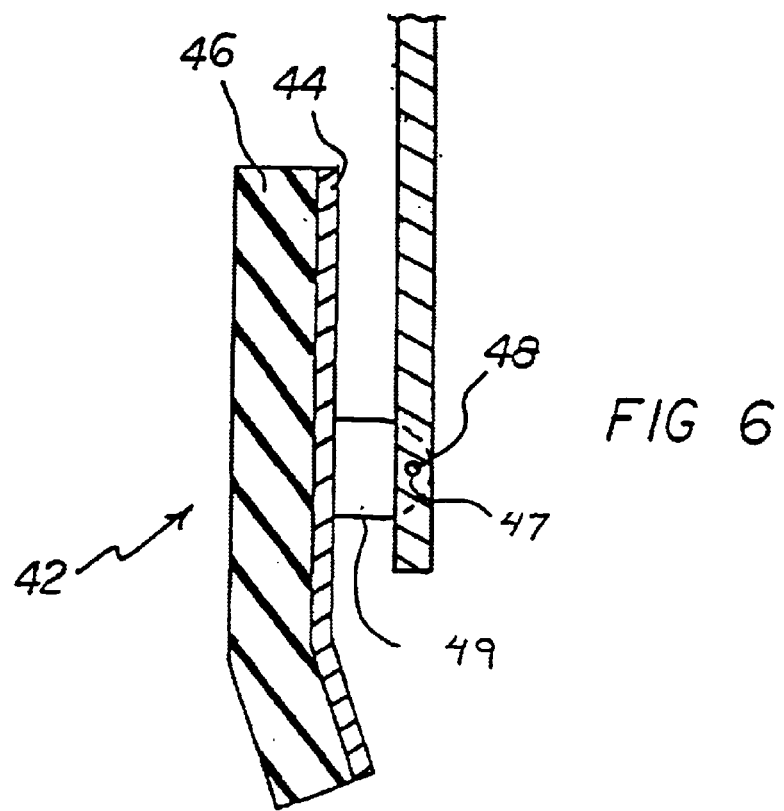
FIG. 6 is a cross sectional view taken along line 6—6 of FIG. 1.
Figure 7:
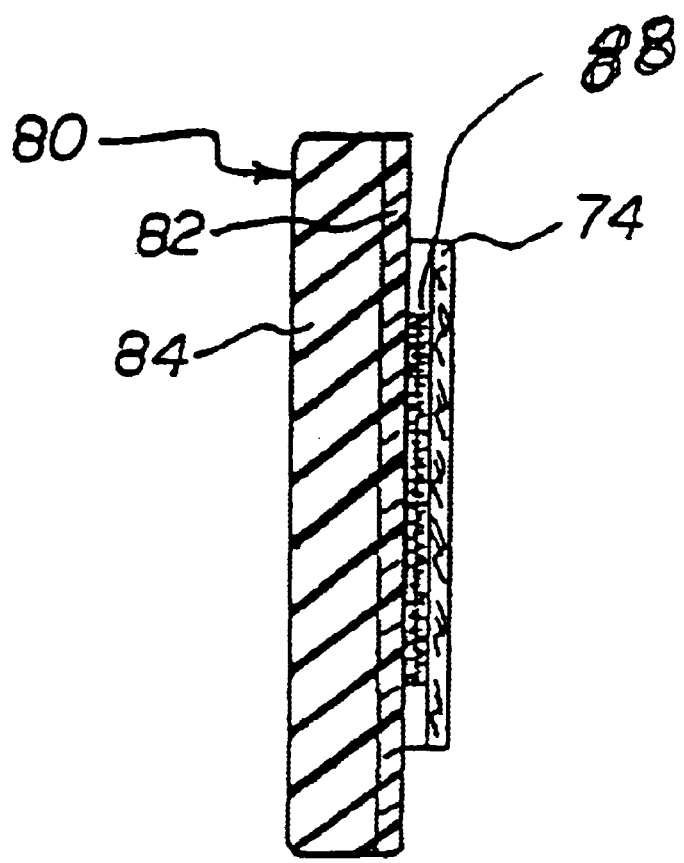
FIG. 7 is a cross sectional view taken along line 7—7 of FIG. 2.

Next provided is a pubic pad 42 formed of a rigid aluminum material 44. The pubic pad has an inwardly facing resilient foam 46 fixedly coupled to the lower end of the lower extender arm. A horizontal pivot pin 48 is located between the pubic pad and the lower extender arm. More specifically, as can be seen in FIGS. 1 and 6, the lower extender arm 28 has a transverse hole 47 there through and the rigid material 44 of the pubic pad 42 has inwardly turned parallel portions 49 with aligned holes 51 spanning the transverse hole 47 with the pivot pin 48 therethrough.

A V-shaped intermediate plate 50 is secured at its central extent to the upper end of the upper extender arm. A pair of diamond-shaped pectoral pads 52 are fabricated of a rigid aluminum material 54. Resilient foam 56 extends inwardly from the pectoral pads. Each pectoral pad is adjustably coupled to a free end 58 of the intermediate plate through a foam rubber disc 60 glued to the pectoral plate for universal swiveling. A first surface of the disc 60 is glued to one of the pectoral pads and a second surface has a pile fastener 62 for coupling the pectoral pads to the V-shaped intermediate plate. The intermediate support is in a V-shaped configuration with upwardly and outwardly extending arms at an angle of about 120 ndegrees plus or minus 10 percent from each other and symmetric with respect to the central axis of the system. The foam rubber discs 60 are resilient to provide for a universal swivel between the pectoral pads 52 and the intermediate plate 50, wherein the inherent sponginess of foam rubber enables a generally full range of resilient motion for pectoral pads 52 relative to intermediate plate 50. This full range of motion, or universal swivel, provides the user with adjustably comfortable pectoral pressure at all angles, an improvement as described elsewhere herein and a feature heretofore unavailable in the art.

A pair of side pads 64 are formed of a rigid material 66. The side pads are fixedly coupled to the exterior end of the horizontal extender arms. The side pads have an inwardly facing resilient foam 68. Each of the side pads has a vertical slot 70, 72 at its free end.

A belt 74 of a pile material is attached at one end 76 through one of the vertical slots 70 of one of the side pads and a free end 78 adapted to be adjustably threaded through one of the vertical slots 72 of the other of the side pads. In this manner the belt is releasably secured around the torso of a wearer.

A back pad 80 is fabricated of a semi-rigid plastic material 82. A resilient foam 84 is provided and faces inwardly from the back pad. Vertical slots 86 are provided in the back pad at laterally disposed end locations adjacent the edges of the back pad for the passage of an intermediate portion of the belt. The back pad also includes a pile fastener 88. An intermediate extent 92 of the belt is adapted to be releasably secured to the pile type fastener on the back pad for the releasable securement. In this manner lateral shifting of the back pad or the belt is precluded.

The purpose of a hyperextension brace is to apply a pressure that tends to extend the spine. If one were to think of someone bending down to pick something up, his or her spine is fully flexed. Think of someone standing very straight with their head back, his or her spine is almost fully extended. The purpose of the hyperextension brace is to hold the spine of a person in this position, more or less. The idea of hyperextension is really a misnomer, but its use is entrenched.

A hyperextension brace is used mostly for old people, primarily women, whose spine is flexed, hunchbacked, or who have sustained an anterior compression fracture, where the bodies of one or more vertebrae have been crushed, thereby losing normal height. In the hunchbacked person, the hyperextension brace provides a force to either straighten the spine or to keep it from flexing any worse. In the person who has a compression fracture, the hyperextension brace provides the same force to maintain normal vertebral body height during bone healing.

All hyperextension braces use a three-point pressure system. There are two posteriorly directed forces, one being the sternal plate, in the present invention the pectoral plates, the other being the pubic plate. There is one anteriorly directed force, that being the belt going around the back in the middle. The side pads of a hyperextension brace are merely there to keep the plates creating those pressures in position.

There are two kinds of hyperextension braces. The first is the Jewett invention, which uses a peripheral frame to attach the plates and pads together. There are a number of variations of this brace in current use.

The second is the brace that was invented by the inventor of the present invention in the 1970n's. It uses a cross structure consisting of a vertical bar and horizontal bar to connect the four plates and pads.

An innovation on that invention is the Houswerth patent where two pectoral plates are used instead of the one sternal plate. This design is an improvement over the original design of the present inventor in that, on many patients, the sternal plate exerts pressure greater than they can tolerate on the sternum. Having two plates that apply pressure on either side of the sternum helps. There are some problems with this design, however, which the current design solves.

There are several significant features of the present invention. They are the top assembly which provides a cosmetic as well as physical improvement, adjustable pectoral plates which as they are adjusted wider get higher and which is a symmetrical vertical bar maintained with a horizontal bar below midline of the brace and an adjustable angle of pectoral plates. The top plate also has anatomically shaped pectoral plates with a universal hinge or swivel, due to the resilience of the rubber discs at each pectoral plate, that is naturally self-centering. Other features are the pile type fastener on the back pad to stop migration of the belt as well as the swivel on the pubic plate stamped out of the plate for economy of manufacture.

The primary advantage of the top piece over of the present invention Houswerth's design is that women, who are the vast majority of the wearers of hyperextension braces, can wear a normal top with the top button unbuttoned, or a v-neck top, without the brace showing. In Houswerth's design, the attachment bar for the pectoral plates must be horizontal because it contains a swivel. If he made those bars to form a "v" like the present invention's design does, then as soon as pressure was applied to the plates, the swivel would be pushed to its top stop and would be rendered useless.

Just like Houswerth's design, the pectoral plates are adjustable, but with his, as you adjust them wider, the brace stays the same height. With the present invention as you adjust the width wider, the height also gets greater, and vice versa. This makes for greater vertical adjustability of the brace.

Since the V-plate attaches the pectoral plates at a height above the top of the vertical bar, the horizontal bar, which attaches to the center of height of the vertical bar, is below the center of height of the brace. This feature allows for more room for sagging breasts, a condition common with elderly women these braces are often fit on.

Because of the pile type attachment of the present invention, the plates can be adjusted both for angle as well as width and height. This is important because these plates, which are anatomically designed to line up along the pectoral musculature groove below the clavicles, can be positioned for the individual patient's clavicle angle.

Houswerth's design uses round plates. The present invention uses plates designed to fit the angles of the side of the sternum, the bottom of the clavicle, and to avoid impinging on the breasts of big-busted women. This design allows one to obtain approximately twice the surface area in the present plates, thus lowering the pressure per square inch. If one used round plates of equal area to the present plates, patients would not tolerate the impingement on the clavicle, sternum, or breasts.

Houswerth's design allows the pectoral plates to swivel in two planes so that they can lie flat on the body. As stated above, in order to achieve this effect, the bar attaching the two pectoral plates had to be horizontal to the vertical bar.

The present design is superior in that there are mounted universal swivels at the point of each pectoral pad, thus allowing the bar that connects them to be v-shaped rather than a straight bar that is horizontal. This gives a big cosmetic advantage, as stated above. Also, the present hinges are rubber discs that allow deflection in two planes, just as Houswerth's do, but the present are self centering. Also, the present invention allows the angle of the pad to go through a few degrees of rotation, but that also is self centering, so that they always return to the position in which they were initially placed.

For some 20 years the brace as disclosed in prior art patents had a back pad that slides on the back strap which constantly migrates out of place by side to side movement. Goins'design attempts to solve this problem by making the strap wider in the middle. This is expensive and inefficient and, probably for that reason, has never been done commercially. The present design contains the simple solution of bonding a pile type fastener coin of hook material onto the outside of the back pad. This stops the migration of the pad on the strap.

Although it is not described in the literature of any of these patents, the braces for years have been offered with a swiveling pubic pad. This is done by riveting a machined stud with a hollowed bore to the pubic pad, drilling a sideways hole through the vertical bar attaching to the pubic pad, punching a square hole in that vertical bar, putting a pin through both the stud and the bar and peening one side of the bar together so the pin stays in place.

The present design is far more economical to manufacture. It consists of punching out flaps when the pubic pad is punched, forming them upwards, drilling the same sideways hole through the bar, and inserting a press-pin through the holes.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A hyperextension back brace system for applying pressure to the pubic area below and to spaced pectoral areas above and to the back thereby tending to extend the spine of a user comprising:

a cruciform structure having an integrally formed upper vertical arm and a lower vertical arm and having an integrally formed left horizontal arm and a right horizontal arm coupled together in a central area, the upper and lower vertical arms each having a longitudinal slot therethrough and the horizontal arms each having a pair of threaded apertures therethrough, an extender arm for each of the arms of the cruciform structure, the extender arms for each of the vertical arms having a pair of threaded apertures with a pair of bolts extending through one of the longitudinal slots for the adjustable coupling with respect to the vertical arms, the extender arms for each of the horizontal arms having a longitudinal slot with bolts therethrough for the adjustable coupling with respect to the horizontal arms;

a pubic pad formed of a rigid aluminum material with an inwardly facing resilient foam fixedly coupled to the lower end of the lower extender arm of the lower vertical arm with a horizontal pivot pin there between;

a V-shaped intermediate plate secured at its central extent to the upper end of the extender arm of the upper vertical arm with a pair of diamond-shaped pectoral pads fabricated of a rigid aluminum material with an inwardly facing resilient foam extending outwardly therefrom, each pectoral pad adjustably coupled to a free end of the V-shaped intermediate plate through a foam rubber disc, a surface of the disc is glued to one of the pectoral pads and another surface includes a pile fastener for coupling the pectoral pads to the V-shaped intermediate plate;

a pair of side pads formed of a rigid plastic material with an inwardly facing resilient foam fixedly coupled to an exterior end of the horizontal extender arms, each of the side pads having a vertical slot at their free ends;

a belt of a pile material attached at one end through one of the vertical slots of one of the side pads and a free end adapted to be adjustably threaded through one of the vertical slots of the other of the side pads for releasably securing the belt around the torso of a wearer; and a back pad fabricated of a semi-rigid plastic material with a resilient foam facing inwardly therefrom, the back pad having vertical slots at laterally disposed end locations adjacent edges of the back pad for the passage of an intermediate portion of the belt there through, the back pad also including a pile fastener and with an intermediate extent of the belt adapted to be releasably secured to the pile fastener on the back pad for the releasable securement there between to thereby preclude lateral shifting of the back pad or the belt.

2. A hyperextension back brace system comprising:

a cruciform structure having an upper vertical arm and a lower vertical arm and having a left horizontal arm and a right horizontal arm, and an extender arm for each of the arms of the cruciform structure;

a pubic pad formed of a rigid material with an inwardly facing resilient foam fixedly coupled to the lower end of the extender arm of the lower vertical arm with a horizontal pivot pin therebetween;

a V-shaped intermediate plate secured at its central extent to the upper end of the extender arm of the upper vertical arm with a pair of pectoral pads fabricated of a rigid material with an inwardly facing resilient foam extending inwardly therefrom, the V-shaped plate having upwardly extending arms at an angle of 120 degrees plus or minus 10 percent;

a pair of side pads formed of a rigid material with an inwardly facing resilient foam fixedly coupled to an exterior end of the horizontal extender arms, each of the side pads having a vertical slot at their free ends;

a belt of a pile material attached at one end through one of the vertical slots of one of the side pads and a free end adapted to be adjustably threaded through one of the vertical slots of the other of the side pads; and a back pad fabricated of a semi-rigid material with a resilient foam facing inwardly therefrom, the back pad having vertical slots at laterally disposed end locations adjacent edges of the back pad.

3. A hyperextension back brace system comprising:

a cruciform structure having an upper vertical arm and a lower vertical arm and having a left horizontal arm and a right horizontal arm, and an extender arm for each of the arms of the cruciform structure;

a pubic pad formed of a rigid material with an inwardly facing resilient foam fixedly coupled to the lower end of the extender arm of the lower vertical arm with a horizontal pivot pin therebetween;

a V-shaped intermediate plate secured at its central extent to the upper end of the extender arm of the upper vertical arm with a pair of pectoral pads fabricated of a rigid material with an outwardly facing resilient foam extending therefrom, each of the pectoral pads being diamond shaped with a foam rubber disc, a surface of the disc is glued to one of the pectoral pads and another surface includes a pile fastener coupled between each foam rubber disc and the V-shaped plate adjacent to the free upper ends thereof;

a pair of side pads formed of a rigid material with an inwardly facing resilient foam fixedly coupled to an exterior end of the horizontal extender arms, each of the side pads having a vertical slot at their free ends;

a belt of a pile material attached at one end through one of the vertical slots of one of the side pads and a free end adapted to be adjustably threaded through one of the vertical slots of the other of the side pads; and a back pad fabricated of a semi-rigid material with a resilient foam facing inwardly therefrom, the back pad having vertical slots at laterally disposed end locations adjacent edges of the back pad.

4. A hyperextension back brace comprising:

a cruciform structure having a first arm and a second arm, wherein said first arm is substantially perpendicular to said second arm, said first arm is carried proximate to a generally central point along a longitudinal axis of said second arm, said first arm has an upper end and a lower end, and said second arm has a first end and a second end, wherein said first arm is worn substantially parallel to a brace wearer's spine, and wherein said second arm is worn substantially perpendicular to a brace wearer's spine;

a V-shaped plate, wherein said V-shaped plate is carried proximate to said upper end of said first arm of said cruciform structure, wherein said V-shaped plate has a first end, a second end, and a central base point therebetween, and wherein said first end and said second end of said V-shaped plate are positioned upwardly of said central base point of said V-shaped plate and upwardly to said upper end of said first arm of said cruciform structure as worn by a brace wearer;

a first pectoral pad and a second pectoral pad, wherein said first pectoral pad is carried proximate to said first end of said V-shaped plate and wherein said second pectoral pad is carried proximate to said second end of said V-shaped plate;

a pubic pad, wherein said pubic pad is carried proximate to said lower end of said first arm of said cruciform structure;

a first side pad and a second side pad, wherein said first side pad is carried by said first end of said second arm and said second side pad is carried by said second end of said second arm;

a first belt receiving member and a second belt receiving member, wherein said first belt receiving member is carried proximate to said first side pad and said second belt receiving member is carried proximate to said second side pad;

a belt, wherein said belt is carried by said first belt receiving member and said second belt receiving member; and, a back pad, wherein said back pad is carried by said belt.

5. The hyperextension back brace of claim 4, wherein said first arm of said cruciform structure comprises at least two elongated members, wherein said at least two elongated members are longitudinally adjustable relative to each other.

6. The hyperextension back brace of claim 4, wherein said first arm of said cruciform structure comprises three elongated members including a first upper member, a second central member and a third lower member, wherein said second central member has at least one aperture defined therein, wherein said first upper member carries at least one locking pin for adjustably fixing the position of said first upper member relative to said second central member, and wherein said third lower member carries at least one locking pin for adjustably fixing the position of said third lower member relative to said second central member.

7. The hyperextension back brace of claim 4, wherein said first arm of said cruciform structure comprises three elongated members including a first upper member, a second central member and a third lower member, wherein said first upper member has at least one aperture defined therein, wherein said third lower member has at least one aperture defined therein, wherein said second central member carries at least one locking pin for adjustably fixing the position of said first upper member relative to said second central member, and wherein said second central member carries at least one locking pin for adjustably fixing the position of said third lower member relative to said second central member.

8. The hyperextension back brace of claim 4, wherein said pubic pad is pivotally carried.

9. The hyperextension back brace of claim 4, wherein said first pectoral pad and said second pectoral pad are each carried via a swivel structure.

10. The hyperextension back brace of claim 9, wherein said swivel structure of said first pectoral pad and said second pectoral pad is self-centering.

11. The hyperextension back brace of claim 4, wherein said first pectoral pad is carried via a first mount and said second pectoral pad is carried via a second mount, wherein each said mount enables substantially universal movement of said first pectoral pad and said second pectoral pad relative to the plane of said V-shaped plate.

12. A hyperextension back brace comprising:

a cruciform structure having a first arm and a second arm, wherein said first arm is substantially perpendicular to said second arm, said first arm is carried proximate to a generally central point along a longitudinal axis of said second arm, said first arm has an upper end and a lower end and said second arm has a first end and a second end; wherein said first arm is worn substantially parallel to a brace wearer's spine, and wherein said second arm is worn substantially perpendicular to a brace wearer's spine;

a V-shaped plate, wherein said V-shaped plate is carried proximate to said upper end of said first arm of said cruciform structure, wherein said V-shaped plate has a first end, a second end, and a central base point therebetween, and wherein said first end and said second end of said V-shaped plate are positioned upwardly of said central base point of said V-shaped plate and upwardly to said upper end of said first arm of said cruciform structure;

a first pectoral pad and a second pectoral pad, wherein said first pectoral pad is carried proximate to said first end of said V-shaped plate, wherein said second pectoral pad is carried proximate to said second end of said V-shaped plate, and wherein said first pectoral pad is carried via a first mount and said second pectoral pad is carried via a second mount, wherein each said mount enables stantially universal movement of said first pectoral pad and said second pectoral pad relative to the plane of said V-shaped plate and wherein each said mount is self-centering;

a pubic pad, wherein said pubic pad is carried proximate to said lower end of said first arm of said cruciform structure;

a first side pad and a second side pad, wherein said first side pad is carried by said first end of said second arm and said second side pad is carried by said second end of said second arm;

a first belt receiving member and a second belt receiving member, wherein said first belt receiving member is carried proximate to said first side pad and said second belt receiving member is carried proximate to said second side pad;

a belt, wherein said belt is carried by said first belt receiving member and said second belt receiving member; and, a back pad, wherein said back pad is carried by said belt.

13. A body brace comprising:

a first pectoral posterior force applicator;

a second pectoral posterior force applicator;

a pubic posterior force applicator;

an anterior force applicator; and, a brace frame for supporting said force applicators, said brace frame having an elongated main support bar with a first end and a second end, wherein said elongated main support bar is worn generally lengthwise on the wearer's body, a central cross bar carried generally perpendicular to and proximate to the approximate midpoint of said elongated main support bar, wherein said central cross bar is worn generally cross-wise on the wearer's body, and an upper cross bar carried proximate to said first end of said elongated main support bar, said upper cross bar generally defining a V-shape having a base proximate to said first end of said elongated main support bar and having two distal ends, wherein said two distal ends of said V-shaped upper cross bar are positioned upwardly of said base of said V-shape upper cross bar and upwardly relative to said first end of said elongated main support bar, wherein said first pectoral posterior force applicator and said second pectoral posterior force applicator are opposingly positioned and are carried via swivelable mount media by said upper cross bar, said pubic posterior force applicator is pivotally carried by said elongated main support bar proximate to said second end thereof, and said anterior force applicator is carried by a strap carried by said central cross bar.

14. The body brace of claim 13, wherein the position of said first pectoral posterior force applicator and said second pectoral posterior force applicator is adjustable relative to said upper cross bar and wherein an increase of distance between said first pectoral posterior force applicator and said second pectoral posterior force applicator results in a relative increase of distance between said pectoral posterior force applicators and said central cross bar.

15. The body brace of claim 13, wherein said swivelable mount media carrying said first pectoral posterior force applicator and said second pectoral posterior force applicator is self-centering.

16. The body brace of claim 13, wherein said elongated main support bar is longitudinally adjustable and said central cross bar is laterally adjustable.

17. A body brace comprising:

a first pectoral posterior force applicator;

a second pectoral posterior force applicator;

a pubic posterior force applicator;

A, an anterior force applicator; and, a brace frame for supporting said force applicators, said brace frame having an elongated main support bar with a first end and a second end, a central cross bar carried generally perpendicular to and proximate to the approximate midpoint of said elongated main support bar, and an upper cross bar carried proximate to said first end of said elongated main support bar, said upper cross bar generally defining a V-shape having a base proximate to said elongated main support bar at a first distance from said central cross bar and having two distal ends at a second distance from said central cross bar, wherein said second distance from said central cross bar is greater than said first distance from said central cross bar, wherein said first pectoral posterior force applicator and said second pectoral posterior force applicator are opposingly positioned and are swivelably carried by said upper cross bar via rubber mounts enabling generally universal, self-centering swivel movement, said pubic posterior force applicator is pivotally carried by said elongated main support bar proximate to said second end thereof, and said anterior force applicator is carried by a strap carried by said central cross bar, and wherein said elongated main support bar is worn generally lengthwise on the wearer's body and said central cross bar is worn generally cross-wise on the wearer's body.

* * * * *